US006770260B1

(12) United States Patent
Chen et al.

(10) Patent No.: US 6,770,260 B1
(45) Date of Patent: Aug. 3, 2004

(54) METHOD PREVENTING DEPLETION OF NON-AUTOLOGOUS HEMATOPOIETIC CELLS AND ANIMAL MODEL SYSTEMS FOR USE THEREOF

(75) Inventors: Ben Chen, Fremont, CA (US); Chris Fraser, Los Altos, CA (US); Irv Weissman, Redwood City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/704,445

(22) Filed: Aug. 26, 1996

Related U.S. Application Data

(63) Continuation of application No. 08/169,293, filed on Dec. 17, 1993, now abandoned.

(51) Int. Cl.[7] .................. A61K 49/00; A61K 48/00; A01K 67/027

(52) U.S. Cl. .................. 424/9.2; 424/93.21; 424/278.1; 800/14

(58) Field of Search .................. 800/2, 8; 424/93.1, 424/9.2, 601, 278.1

(56) References Cited

PUBLICATIONS

Alamondi et al Nature 363: 732, 1993.*
Baum, et al PNAS 89: 2804, 1992.*
Bernsen et al J. Clin Invest, 88: 540, 1988.*
Bernsen et al Blood 77(8): 1717, 1991.*
Pinto et al J. Leukocyte Brief 49: 579, 1991.*
*Immunology*, Kaby, pp. 488–494, 1992, W.H. Freeman and Company, NY, Sep. 25, 1997.*
Phyrenia et al, Orkansival Immunology, 5(12): 1509, 1993, Sep. 25, 1997.*
Sykes et al. "Bone Marrow transplantation as a means of inducing tolerance," Seminars in Immunology, vol. 2: 401–417, 1990.*
Smith et al. "New Approaches to Transplantation Tolerance," vol. 23 (4): 2157–2161, 1991.*
Mosier et al., "Transfer of a functional human immune system to mice with severe combined immunodeficiency" *Nature* (1988) 335:256–259.
Kamel–Reid et al., "Engraftment of immune–deficient mice with human hematopoietic stem cells" *Science* (1988) 242:1706–1709.
McCune et al., "The SCID–hu mouse: murine model for the analysis of human hematolymphoid differentiation and function" *Science* (1988) 241:1632–1639.
Namikawa et al., "Long–term human hematopoiesis in the SCID–hu mouse" *J. Exp. Med.* (1990) 172:1055–1063.
Kyoizumi et al., "Implantation and maintenance of functional human bone marrow in SCID–hu mice" *Blood* (1992) 79:1704–1711.

Lapidot et al., "Cytokine stimulation of multilineage hematopoiesis from immature human cells engrafted in SCID mice" *Science* (1992) 255:1137–1141.
Krowka et al., "Human T cells in the SCID–hu mouse are phenotypically normal and functionally competent" *J. Immunol.* (1991) 146:3751–3756.
Vanderkerckhove et al., "Clonal analysis of the peripheral T cell compartment of the SCID–hu mouse" *J. Immunol.* (1991) 146:4173–4179.
Vanderkerckhove et al., "Human hematopoietic cells and thymic epithelial cells induce tolerance via different mechanisms in the SCID–hu mouse thymus" *J. Exp. Med.* (1992) 175:1033–1043.
Péault et al., "Lymphoid reconstitution of the human fetal thymus in SCID mice with CD34+ precursor cells" *J. Exp. Med.* (1991) 174:1283–1286.
Baum et al., "Isolation of a candidate human hematopoietic stem–cell population" *Proc. Natl. Acad. Sci. USA* (1992) 89:2804–2808.
McCune et al., "Suppression of HIV infection in AZT–treated SCID–hu mice" *Science* (1990) 247:564–566.
Lockwood, "Immunological functions of the spleen" *Clin. Haematol.* (1983) 12:449–465.
Van Rooijen et al., "Elimination of phagocytic cells in the spleen after intravenous injection of liposome–encapsulated dichloromethylene diphosphonate" *Cell Tiss. Res.* (1984) 238:355–358.
Gregoriadis et al., eds., *Targeting of Drugs*, Plenum Press, New York (1982). A title page and table of contents is enclosed herewith.
Van Rooijen et al., "Macrophage subset repopulation in the spleen: Differential kinetics after liposome–mediated elimination" *J. Leuk. Biol.* (1989) 45:97–104.
Oi et al., "Fluorescent phycobiliprotein conjugates for analyses of cells and molecules" *J. Cell Biol.* (1982) 93:981–986.
Boorsma et al., "Periodate or glutaraldehyde for preparing peroxidase conjugates?" *J. Immunol. Met.* (1979) 30:245–255.
Eikelenboom, "Characterization of non–lymphoid cells in the white pulp of the mouse spleen: An in vivo and in vitro study" *Cell Tiss. Res.* (1978) 195:445–460.
Delemarre et al., "The in situ immune response in popliteal lymph nodes of mice after macrophage depletion. Differential effects of macrophages on thymus–dependent and thymus–independent immune responses" *Immunobiol.* (1990) 180:395–404.

(List continued on next page.)

Primary Examiner—Ram R. Shukla
(74) Attorney, Agent, or Firm—Fish & Neave

(57) ABSTRACT

The invention provides methods for preventing depletion of non-autologous hematopoietic cells. Animal model systems using the method are also provided as are methods of treatment using non-autologous hematopoietic cells.

19 Claims, 6 Drawing Sheets

OTHER PUBLICATIONS

Van Rooijen, "The liposome–mediated macrophage 'suicide' technique" *J. Immunol. Meth.* (1989) 124:1–6.

Berenson et al., "Engraftment after infusion of CD34+ marrow cells in patients with breast cancer or neuroblastoma" Blood (1991) 77:1717–1722.

Pinto et al., "Selective depletion of liver and splenic macrophages using liposomes encapsulating the drug Dichloromethylene Disphosphonate: Effects on antimicrobial resistance" *J. Leuk. Biol.* (1991) 49:579–586.

Huppes et al.,"The role of natural antibodies and ABO (H) blood groups in transplantation of human lymphoid cells into mice." *Eur. J. Immunol.* (1993) 23:26–32.

Bleeker et al., "Key role of macrophages in hypotensive side effects of immunoglobulin preparations. Studies in an animal model." *Clin. exp. Immunol.* (1989) 77:338–344.

McCune et al., "The SCID–hu mouse as a model system for HIV infection." UCLA Symposia on Molecular and Cellular Biology, New Series, *Human Retroviruses* (1990) Alan R. Liss, Inc., vol. 119, pp. 347–359.

Peault, B.M. et al., "Surface marker for hemopoietic and endothelial cell lineages in quail that is defined by a monoclonal antibody" Proceedings of the National Academy of Sciences of USA 80(10): 2976–2980 (1983).

Tsukamoto, A. et al., "Characterization and enrichment of canditate human hematopoietic stem cells" J. of Hematotherapy 2(1): 117–119 (1993).

* cited by examiner

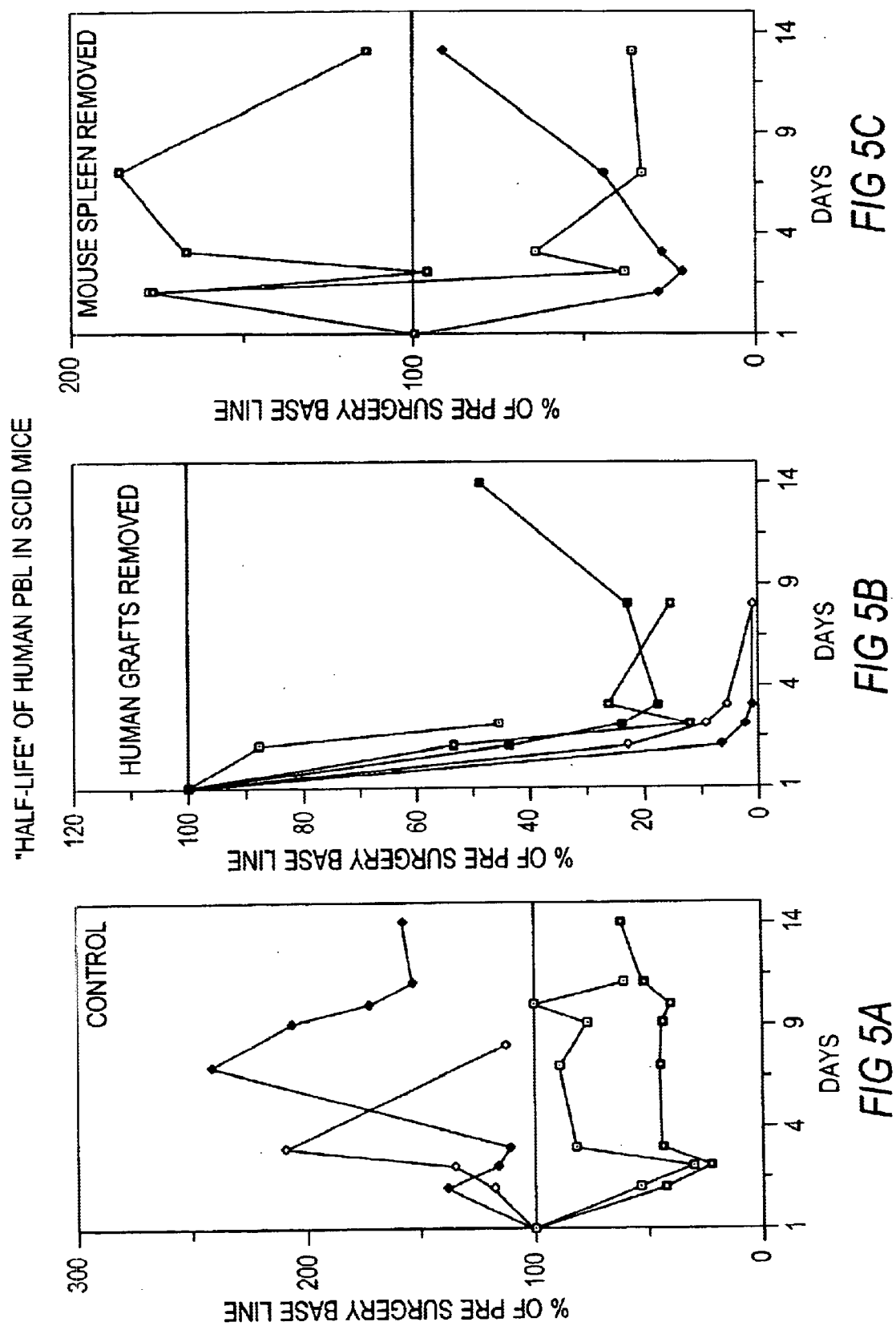

METHOD PREVENTING DEPLETION OF NON-AUTOLOGOUS HEMATOPOIETIC CELLS AND ANIMAL MODEL SYSTEMS FOR USE THEREOF

This application is a continuation of application Ser. No. 08/169,293, filed 17 Dec. 1993, now abandoned.

TECHNICAL FIELD

The invention is in the field of hematopoietic cell reconstitution.

BACKGROUND ART

Animals including man tend to deplete rapidly non-autologous peripheral hematopoietic cells. This is true even if the animals are immunocompromised. This phenomenon has hindered the use of allogeneic cell transfusions in immunocompromised humans. Animal model systems have been proposed to study the human hematopoietic and immunologic system. However, they are not adequately reflective of the full complement of the immune system due to the lack or decreased amount of xenogeneic peripheral hematopoietic cells.

The most frequently used animal models of the human immune system utilize severe combined immune deficiency (SCID) mice that have been injected with human peripheral blood cells or bone marrow cells; or that have been humanized by co-implantation of human fetal thymus and liver (Thy/Liv) or by implantation of human fetal bone marrow fragments. Mosier et al. (1988) Nature, 335:256; Kamel-Reid and Dick (1988) Science, 242:1706; McCune et al. (1988) Science, 241:1632; Namikawa et al. (1990) J. Exp. Med., 172:1055; Kyoizumi et al. (1992) Blood, 79:1704; Kyoizumi (1993) Blood, 81:1497; and Namikawa et al. (1993) Blood, 82:2526. Injection of human bone marrow followed by a regimen of cytokine injections has been shown to allow substantial prolongation of survival of human myeloid progenitors. Lapidot et al. (1992) Science, 255:1137. The SCID-hu Thy/Liv grafts produce phenotypically normal human T cells in the periphery for prolonged periods, allowing mechanisms of tolerance induction and T cell repertoire to be studied. Krowka et al. (1991) J. Immunol., 146:3751; Vandekerckhove et al. (1991) J. Immunol., 146:4173; Vandekerckhove et al. (1992) J. Exp. Med., 175:1033; Vandekerckhove et al. (1992) J. Exp. Med., 176:1619; and Baccala et al. (1993) J. Exp. Med., 177:1481.

SCID-hu mice are also valuable for the study of human hematopoietic stem cell development and human immunodeficiency virus (HIV) pathogenesis. Peault et al. (1991) J. Exp. Med., 174:1283; Baum et al. (1992) Proc. Natl. Acad. Sci. USA, 89:2804; McCune et al. (1990) Science, 247:564; Bonyhadi et al. (1993) Nature, 363:728; Aldrovandi et al. (1993) Nature, 363:732; and copending co-owned U.S. patent application Ser. No. 07/882,937.

The potential use of SCID-hu mice is limited, however, by the low engraftment of human cells. The current models would be greatly improved by providing a means to allow human hematopoietic cells to survive and circulate freely in the periphery of immunocompromised mice. Moreover, methods useful in increasing engraftment of human cells in SCID-hu mice have direct application in a variety of human disorders.

The mononuclear phagocyte systems of the spleen and liver are important sites of phagocytosis of both opsonized and non-opsonized particles as well as in the early phases of bacterial infection. Lockwood (1983) Clin. Hematol. 12:449. Specific elimination of macrophages in the spleen and liver can be effected by injection of liposome-encapsulated dichloromethylene diphosphonate ($Cl_2MDP$). Van Rooijen et al. (1984) Cell Tissue Res., 238:355; and Van Rooijen and Claasen, In vivo Elimination of Macrophages in Spleen and Liver, Using Liposome-Encapsulated Drugs: Methods and Applications (John Wiley and Sons, Chichester, 1988). Injection of free $Cl_2MDP$ does not result in significant macrophage depletion because small, charged molecules like $Cl_2MDP$ are not subject to endocytosis by macrophages as liposomes are. Gregoriadis et al., Targeting of Drugs (Plenum Press, New York, 1982). Nor does the injection of liposome-encapsulated phosphate-buffered saline (PBS) reduce macrophage levels as neither the liposomes nor the PBS are toxic to the macrophage. However, a single intravenous injection of liposome-encapsulated $Cl_2MDP$ results in the disappearance of splenic red pulp and marginal zone macrophages with recovery of these subpopulations occurring 1–2 weeks and greater than one month respectively. Van Rooijen et al. (1989) J. Leuk. Biol., 45:97. The $Cl_2MDP$-induced macrophage depletion can be sustained for prolonged periods (at least one month) with sequential intravenous injections. Kraal et al. (1993) Int. Arch. Allergy Immunol., 100:115.

It has now been found that the macrophages in the mononuclear phagocytic system play an important role in clearance of non-autologous hematopoietic cells and elimination of endogenous macrophages results in the ability of non-autologous hematopoietic cells to circulate and survive in the periphery of host animals.

SUMMARY OF THE INVENTION

Methods are provided for preventing depletion of peripheral non-autologous hematopoietic cells in animals including humans by substantially ablating the endogenous macrophage population. Animal models of peripheral non-autologous hematopoietic cells and the full complement of the human hematopoietic system are provided.

BRIEF DESCRIPTION OF THE DRAWINGS

FIG. 4 depicts immunohistochemical and flow cytometric evaluation of macrophage depletion and human cell infiltration in liposome-encapsulated $Cl_2MDP$ treated SCID-hu Thy/Liv mice.

FIG. 5 is 3 graphs depicting the level of human hematopoietic cells in the peripheral blood of SCID-hu Thy/Liv mice.

FIG. 5A depicts the initial transient increase, of human hematopoietic cells after the Thy/Liv transplant. FIG. 5B depicts the decrease in human hematopoietic cells after the human grafts are removed.

FIG. 5C depicts the transient increase of human cells upon removal of the spleen from SCID-hu Thy/Liv mice.

Modes of Carrying Out the Invention

Figure 1:
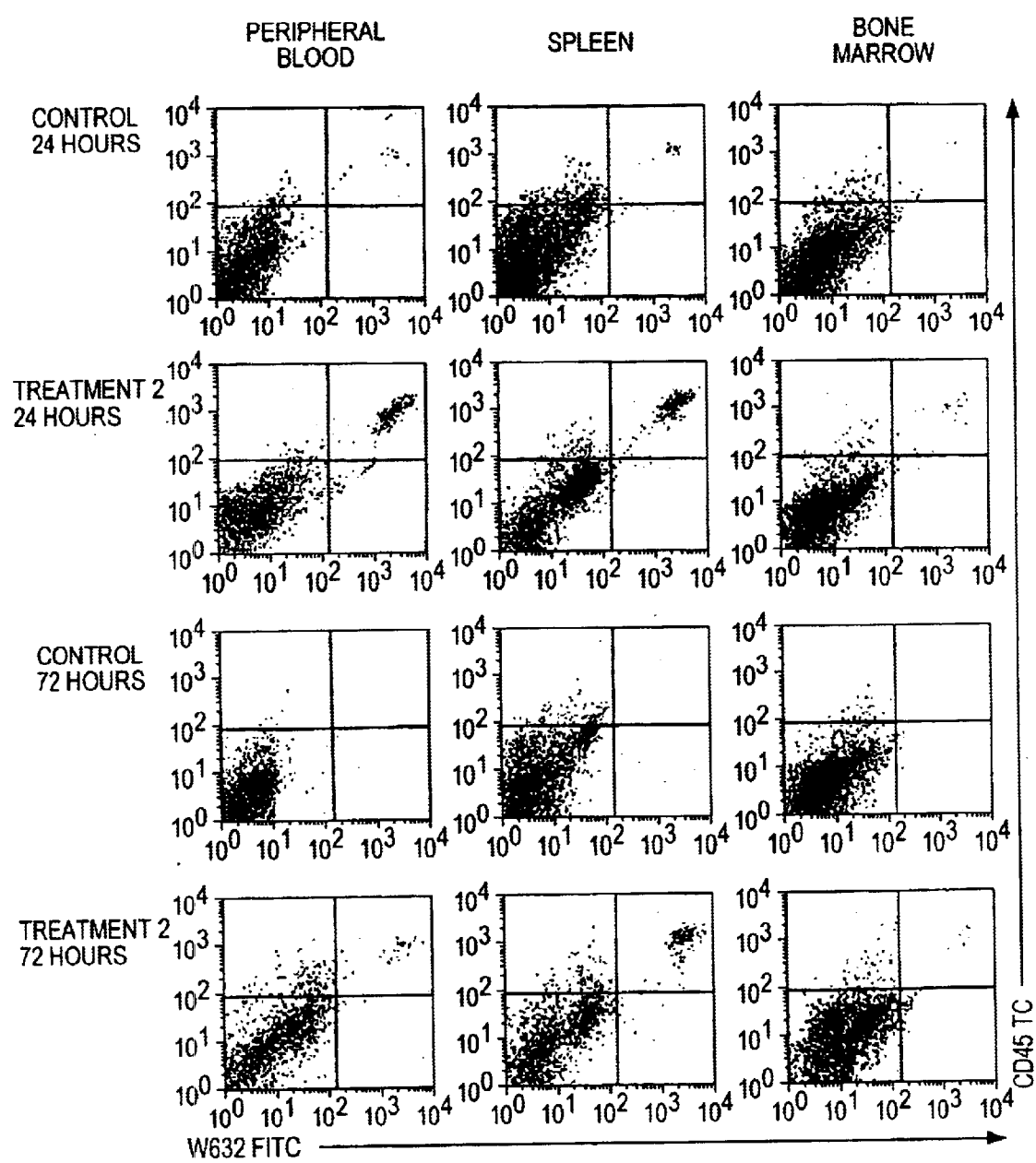
FIG. 1 depicts flow cytometric analyses of peripheral blood, spleen and bone marrow of individual SCID mice either non-treated (control) or treated with liposome-encapsulated $Cl_2MDP$ and injected with human Ficoll-purified peripheral blood leukocytes (Treatment 2) as described in Example 6 and Table 1.

The results described herein indicate that macrophages in the mononuclear phagocytic system play an important role in the clearance of hematopoietic cells in non-autologous animals, and the elimination of macrophages results in the ability of non-autologous hematopoietic cells to circulate and survive in the periphery. Human hematopoietic cells were completely undetectable in peripheral blood, spleen and bone marrow of normal SCID mice when $5 \times 10^6$ human peripheral blood lymphocytes (PBLS) were injected intravenously (i.v.) and mice were analyzed 72 hours later for cells positive for human HLA class I and CD45 by FACS. In contrast, human hematopoietic cells were readily detected in mice pre-treated with liposome-encapsulated $Cl_2MDP$ 72 hours after injection of human PBLs. In addition, a single injection of liposome-encapsulated $Cl_2MDP$. into SCID-hu Thy/Liv mice resulted in an increase of human hematopoietic cells circulating in mouse peripheral blood for at least 2 weeks after the injection.

Histochemical analyses of splenic tissue of SCID mice treated with liposome-encapsulated $Cl_2MDP$ demonstrated a correlation between elimination of acid phosphatase positive cells in the red pulp and marginal zones of the spleen and accumulation of $CD45^+$ cells in the white pulp. Intravenous treatment with liposome-encapsulated $Cl_2MDP$ eliminates phagocytic cells in organs with open circulation, such as the spleen and liver, (Van Rooijen et al. 1984) but does not eliminate splenic white pulp macrophages in normal mice or in SCID mice as described here, presumably since the microcirculation in the white pulp region of the spleen does not allow immediate access to liposomes entering the spleen.

The invention provides methods of preventing depletion of non-autologous hematopoietic cells in animals including man. Non-autologous hematopoietic cells include all hematopoietic cells not produced by the animal itself (the host animal). Hematopoietic cells are those cells derived from hematopoietic stem cells and include, but are not limited to, B cells, T cells, natural killer cells, dendritic cells, macrophages, monocytes, mast cells, granulocytes and megakaryocytes. Non-autologous cells include both allogeneic and xenogeneic cells. The non-autologous cells have now been found to remain in the periphery of the host animal for a longer duration than the times obtained with previous methods. The periphery of the host animal includes, but is not limited to, blood circulation, thymus, tissues, bone marrow and secondary lymphoid tissues. The methods involve decreasing the endogenous macrophages of the animal to a level effective to substantially prevent depletion of the non-autologous cells. The non-autologous hematopoietic cells may be directly injected into the animal or may be produced in the animal by engrafted hematopoietic tissue.

Depletion of endogenous macrophages can be effected by any method known in the art, including, but not limited to, the transgenic elimination or inactivation of macrophages, treatment with L-leucine methyl ester, and the administration of colloidal carbon to the reticuloendothelial system. Preferably, the animals are administered an agent or drug that specifically eliminates macrophages. More preferably, the agent is liposome-encapsulated $Cl_2MDP$. Alternatively, the macrophages are depleted genetically such as by producing an animal that does not produce or produces diminished levels of macrophages, or functionally inactive macrophages.

The methods are also suitable for use in immunocompromised animals to prolong survival of non-autologous hematopoietic cells. Suitable immunocompromised animals include, but are not limited to, humans, SCID mice, SCID-hu mice, CID horse, and transgenic immunodeficient mice. Suitable immunodeficient mice include, but are not limited to, Class I, Class II MHC, Bcl⁻2 proto-oncogene deficient mice and RAG deficient mice. RAG-1 or RAG-2 deficient mice lack the VDJ-recombinase activator genes. Immunocompromised humans include, but are not limited to, those infected with HIV, those undergoing cellular ablative therapy including, but not limited to, radiation and chemotherapy, and humans suffering from SCID.

Preferably, the method is used in SCID mice and the non-autologous hematopoietic cells are human. More preferably, the SCID mice have been engrafted with at least one human hematopoietic tissue which tissue produces the peripheral hematopoietic cells. Suitable tissue for engraftment includes but is not limited to thymus, liver, bone marrow, spleen and lymph nodes, and combinations thereof. Alternatively, the SCID mice may be injected directly with human hematopoietic cells, in conjunction with decreasing the endogenous macrophages. "In conjunction with" means that the endogenous macrophages an be depleted before, during after inducing expression of or directly injecting non-autologous hematopoietic cells.

The method is also suitable for use in humans, particularly those infected with HIV who lack certain subsets of PBLs such as $CD4^+$ lymphocytes. In these persons, an effective amount of human hematopoietic blood cells can be administered to the patient in conjunction with decreasing the endogenous macrophages. The hematopoietic blood cells are preferably hematolymphoid, more preferably T cells and most preferably, $CD4^+$ lymphocytes. These cells may be injected directly into the bloodstream, for instance by intravenous injection, in conjunction with decreasing the endogenous macrophages. In addition the method can be used to reduce endogenous macrophages in HIV patients receiving bone marrow transplantation therapy to increase the survivorship of the engrafted tissue.

The invention further encompasses the reduction of macrophages as a means of improving engraftment efficiency for allogeneic and xenogeneic stem cell transplantation. Improving engraftment efficiency for transplantation of a population of non-autologous hematopoietic stem cells in a host animal includes the steps of ablating, in whole or in part, the endogenous stem cell population of the host animal and transplanting the stem cells into the patient in conjunction with decreasing endogenous macrophages in the host animal. Methods of obtaining populations of hematopoietic stem cells are known in the art as are methods of performing stem cell transplantations.

The non-autologous hematopoietic cells may be derived from any source. In the case of animal model systems, it is preferred that these cells are of human origin so as to more clearly define the human hematopoietic system. In the case of immunocompromised humans, it is preferred to use human cells, preferably those that are as closely histocompatibility matched to the patient as possible.

The non-autologous hematopoietic cells may contain the full complement of peripheral blood elements (PBE) or may comprise one or more subsets thereof. Normally, PBEs include, but are not limited to, red blood cells, lymphocytes, monocytes, and granulocytes. Any one of these subsets or a constituent thereof may also be used, such as discussed above for treatment of HIV-infected persons. Prior to introduction into the host animal, the hematopoietic cells can be separated into their different types by a variety of methods known in the art. These methods include, but are not limited to, flow-cytometry, immunoaffinity with antibodies to hematopoietic cells (chromatography and panning), counterflow centrifugation, separation by density gradients (like ficoll) and elutriation.

Typically, the non-autologous hematopoietic cells are introduced by intravenous injection. In the mouse, such injections are generally into the tail vein; in humans intravenous administration is by methods known in the art. If the cells have been separated, they should be resuspended in a suitable amount of a physiologically acceptable buffer. Such buffers are known in the art and are suitably, sterile, non-pyrogenic and isotonic.

Decreasing the number of endogenous macrophages can be done by any method known in the art. Preferably, the macrophages are decreased by administration of an agent which selectively kills macrophages. For instance, see, Van Rooijen and Claasen (1988). More preferably, $Cl_2MDP$ is administered in a manner whereby it is taken up by macrophages but not other cell types. Typically, the $Cl_2MDP$ is encapsulated in liposomes. Methods of making liposome drug delivery vehicles are known in the art and are not described in detail herein. Such methods include, but are not limited to, the method described briefly in Example 6. Any method of forming liposomes that allows encapsulation of an effective amount of the agent is suitable for use in the present invention.

The effective amount of the agent is that which decreases the level of endogenous macrophages to a level effective to substantially prevent depletion of the non-autologous hematopoietic cells. In the case of liposome-encapsulated $Cl_2MDP$, the effective concentration in mice (both wild type and SCID) is in the range of 0.005 to 0.010 ml of liposomes (containing 23.5 mg/ml lipid per 10 to 15 mM $Cl_2MDP$) per gram of mouse weight. While extrapolating to humans is not directly proportional, typically, the effective range would be 5 to 10 ml of these liposomes per kg of human weight. Other macrophage-toxic substances will have different effective amounts but a determination of the effective amount is within the skill of one in the art. While the determination of an effective amount of a particular agent will be empirical, the effective amount can be determined empirically by monitoring survival of non-autologous hematopoietic cells in the periphery of the host animal. Preferably, the effective dosages are first determined in mice and extrapolated to humans for subsequent preclinical testing.

Substantially preventing depletion of non-autologous hematopoietic cells indicates that for at least several days, and preferably up to several weeks, the cells are found in the peripheral blood of the animal. Preferably 1% of the cells remain in the periphery after several days. More preferably 5% of the cells remain in the periphery after several days. Most preferably 10% of the cells remain in the periphery after several days.

Measurement of the number of non-autologous hematopoietic cells remaining in the periphery in order to determine the effectiveness of the agent can be accomplished by any method known in the art. Such methods must be merely able to distinguish between autologous and non-autologous cells. A variety of such markers are known in the art. In the case of xenogeneic cells, species. specific cell surface markers including, but not limited to, histocompatibility markers can be used. In the case of allogeneic cells, markers including, but not limited to, histocompatibility antigens can be used.

The endogenous macrophages found in the red pulp area of the spleen appear to be responsible for depletion of the non-autologous hematopoietic cells. Therefore the level of these macrophages is preferentially decreased. Nonetheless, the invention is not limited to any particular mechanism of action of the agent; thus agents which kill all macrophages or at least one subset thereof are suitable for use in the present invention provided they substantially prevent depletion of non-autologous hematopoietic cells.

The invention further provides methods of treating animals including humans by administering non-autologous hematopoietic cells and decreasing endogenous macrophages to a level sufficient to prevent substantial depletion of the non-autologous cells. Such treatment is particularly effective for immunocompromised patients as discussed above. The methods of administration are as discussed above.

The invention further provides non-human animal model systems of non-autologous hematopoietic systems. These animals comprise engrafted human hematopoietic tissue and have a decreased level of macrophages sufficient to prevent substantial depletion of human hematopoietic cells. Preferably, the animals are immunocompromised and include, but are not limited to, SCID-hu and SCID-hu Thy/Liv mice. The methods of engraftment and depletion of endogenous macrophages are as discussed above and in the examples presented herein.

The ability to enhance and prolong circulation of human hematopoietic cells in the SCID mouse with prolonged $Cl_2MDP$-liposome treatment increases the potential for study of human hemopoietic, immunologic and disease processes in vivo. Applications include, but are not limited to, vaccine development, immunologic reactions to tumors and the development of human hybridomas.

Prolonged circulation of human hematopoietic cells in the periphery provides a means for human hematopoietic cell function to be studied in vivo such as homing, engraftment, and tumor or allogeneic rejection of foreign tissues which were previously not feasible, or more difficult. Examples include, but are not limited to, the pathogenesis of HIV where the kinetics of infection of a few circulating infected cells may be followed in the SCID-hu Thy/Liv HIV model. Maintenance of human bone marrow or circulating PBEs for longer periods should improve engraftment potential of these populations, and decrease the cell dose required for engraftment making it possible to study development of defined human hemopoietic cell subtypes such as purified stem cells. Finally, the ability of increased numbers of human cells to circulate may allow propagation of cells from tumors or proliferative disorders such as acute or chronic myeloid leukemia which have been difficult to maintain in mice.

The following examples are meant to illustrate but not limit the invention.

EXAMPLES

Example 1

Mice

CB-17 scidlscid (SCID) mice were obtained from Dr. Leonard D. Shultz of the Jackson Laboratory, Bar Harbor, ME. The mice were housed in standard isolator cages within a routine animal holding facility. Under these conditions, they have exhibited a life span that was considerably shorter than that of inbred immunocompetent strains (e.g., 1–2 years vs. 3–4 years). The cause of death was normally related to opportunistic infection (most often by Pneumocystis carinii). To prevent infections, an antibiotic prophylaxis of trimethoprim/sulfamethoxasole (40 mg/200 mg per 5 ml of suspension; 0.125 ml of suspension per 4 ml of drinking water per mouse per day) was administered. In all other respects (e.g., bedding, food, daily light cycles, etc.), the mice were handled as per routine animal holding facility protocols.

Example 2

Collection and Preparation of Fetal Tissue

Tissue samples were obtained from human fetuses under about 24 weeks gestational age that were normal (absent any evidence of chromosomal defects, anencephaly, hydrops, etc. as demonstrated by any available amniotic fluid analysis and/or ultrasonography data). Tissue samples were obtained directly in the operating room as fetal parts after an elective or medically-induced abortion. Without maintaining strict sterility, these parts were taken immediately to a gross dissection room. The fetal liver and thymus were identified, dissected out, and placed into RPMI 1640 medium with 10% fetal calf serum for transport to another lab. The fetal liver fragments were cut into sections of approximately 4 mm×6 mm, to contain all of the representative cells of this organ (microenvironmental stromal cells, hematopoietic stem cells and their progeny, as well as hepatocytes). The fetal thymus fragments were cut into sections of approximately 2 mm×2 mm. These tissues were normally introduced in as fresh a state as possible. Therefore, the tissue collection, preparation and implantation were done all on the same day. Implantation experiments using frozen tissues, however, worked well in the case of fetal liver cells and fetal thymus tissue. Therefore, aliquots of any remaining tissue were frozen in a 10% DMSO, 50% fetal bovine serum (FBS) in RPMI media, using standard procedures, and stored in a liquid nitrogen freezer.

Example 3

Transplantation of Human Tissue into SCID Mice

Generally SCID mice of 4–8 weeks of age were used for fetal tissue transplantation. The mice were anesthetized with ketamine, a 1 cm incision was made to expose the kidney, and the fetal liver and thymus tissue fragments were introduced, by means of a 19 gauge trocar, beneath the kidney capsule. The fragments were placed in close proximity so as to be in contact. Thereafter, the incision was approximated with surgical sutures. CB-17 SCID mice which received fetal human liver and thymus tissue transplants, as described above, were designated SCID Thy/Liv mice. After the experiments described below were performed, the mice were dissected and it was found that they all had large thy-liv grafts approximately the same size as the kidney.

Example 4

Analysis of SCID-hu Thy/Liv Mouse Tissues

A. Immunophenotyping of Peripheral Blood Cells

Peripheral blood samples were collected by tail vein incision or retroorbital bleeding, and approximately 100 µl of whole blood was obtained, usually containing 1 to $2\times10^5$ cells. Nucleated cells were enriched by precipitation of red blood cells with dextran sulfate, or by lysis of red blood cells with hypotonic shock, and washed free of platelets. Cells obtained from tissue samples of the thy-liv grafts, spleen and bone marrow were also analyzed. The cells were resuspended in fluorescent phycobiliprotein conjugates for analyses of cells and molecules (J. Cell Biol. 93:–986), centrifuged at 200 xg, and the red blood cells lysed with hypotonic shock. The remaining cells were washed twice, incubated for 10 min with 1 mg/ml human γ-globulin (Gamimune, Miles Inc, Elkhart, Ind.) and stained as described below.

The cells were transferred to 96-well microtiter plates and stained with tri-color (TC) conjugated monoclonal antibodies to pan-human leukocyte marker CD45 (Caltag) and FITC-conjugated monoclonal antibodies to pan-human HLA class I marker W6/32 (derived from the W6/32 hybridoma obtained from ATCC). FITC conjugation is known in the art. Oi et al. (1982).

The staining was performed as follows: Cells were incubated in 10 µl of staining buffer (PBS with 0.2% bovine serum albumin (BSA) and 0.02% sodium azide) plus30 µg/ml FITC-conjugated W6/32 antibodies, Tricolor-conjugated antibodies to CD45 diluted 1:45 (Caltag) and Ly5.1 purified from ascites were conjugated to biotin succinimide ester and were used at 1–5 µg/ml. Cells were incubated on ice for 20 minutes, followed by 2 washes with staining buffer. Cells were resuspended in 10 µl of staining buffer containing PE-conjugated streptavidin diluted ¹⁄₄₀ (Becton Dickinson) and incubated on ice for 20 minutes. Cells were washed twice with staining buffer and resuspended in 300 µl of fresh staining buffer for analysis. Stained samples were then analyzed on a FACScan fluorescent cell analyzer (Becton Dickinson) for cells positive for both W6/32 and CD45 after gating on cells with lowforward and side scatter properties. In this manner, the human cell content of peripheral blood was determined as a function of total mononuclear cells.

Blocks of fresh splenic tissue were frozen in liquid nitrogen and stored at –70° C. Cryostat sections of 8–10 Am thickness were fixed in acetone for 10 min. and air-dried for at least 30 min. After washing in 0.01 M PBS (pH 7.4) the sections were incubated with the anti-human CD45 monoclonal antibody (clone CLB-T200) which had been conjugated to horse radish peroxidase (HRP) using periodate according to the method described by Boorsma and Streefkerk, (1979) *J. Immunol. Met.,* 30:245. After washing, the peroxidase activity was determined with 3,3'-diaminobenzidine tetrahydrochloride (DAB, Sigma) in 0.5 mg/ml Tris HCl buffer (pH 7.6) containing 0.01% $H_2O_2$. The sections were stained for 10 min. at room temperature. Acid phosphatase in the cryostat sections was determined according to the method described by Eikelenboom (1978) *Cell Tissue Res.,* 195:445.

Example 5
Analysis of Human PBL Half-Life in SCID-hu Thy/Liv Mice

Initial studies indicated that the spleen may play a role in the depletion of human PBLs in SCID-hu mice. FIG. 5 shows the level of human PBLs in SCID-hu mice under varying conditions. The cells were measured as described in Example 4. FIG. 5A shows the initial production of human PBLs in SCID-hu Thy/Liv mice at more than three months after transplantation of the thymus and liver fragments. FIG. 5B depicts the rapid drop in concentration of human cells after the human grafts are removed. FIG. 5C shows a transient increase in peripheral human cells upon removal of the spleen from three to six month old SCID-hu Thy/Liv mice.

The results indicate that spleen removal results in a transient increase of human cells in some of the mice but the increase is not sustained. Example 6
Effects of $Cl_2MDP$ Injection In order to determine the effect of depletion of murine macrophages on the ability of human cells to survive and circulate in vivo in SCID mice, a titration experiment was performed.

Liposome-encapsulated $Cl_2MDP$ was the generous gift of Dr. Nico Van Rooijen. It was prepared with phosphatidyl choline and cholesterol according to the method described by Delemarre et al. (1990) *Immunobiol.* 180:395–404; and Rooijen (1989) *J. Immunol. Meth.* 124:1–6. Briefly, 75 mg phosphatidyl choline and 11 mg cholesterol (Sigma) were dissolved in chloroform in a round bottom flask. After low vacuum rotary evaporation autologous at 37° C. the lipids were dispersed by gentle rotation in 10 ml PBS in which 1.89 g dichloromethylene diphosphonate (Boehringer Mannheim, FRG) was dissolved. The resulting liposomes were washed twice at 100,000 xg for 30 min. to remove free, non-encapsulated $Cl_2MDP$. The liposomes were then suspended in 4 ml of PBS to yield a "100% stock." $Cl_2MDP$ was a gift of Boehringer Mannheim GmbH, Mannheim, Germany. Phosphatidylcholine (Lipid EPC), for preparation of the liposomes was a gift of LIPOID KG, Ludwigshafen, German.

Groups of four, 12 week old SCID mice received one initial, primary, injection of 200 μl 100% stock or 200 μl of 100% stock diluted in PBS immediately prior to injection. Three subsequent injections of 200 μl were given every 5–7 days as shown in Table 1. Four days after the final injection all treated mice and one group of 4 control untreated mice received 5.6 x 10$^6$ Ficoll purified human PBLs. Two mice from each treatment group were then sacrificed 24 hours and 72 hours later for analysis.

TABLE 1

| | Liposome Concentration | |
|---|---|---|
| Treatment | Primary Injection | Subsequent Injections |
| 1 | 100% | 50% |
| 2 | 50% | 25% |
| 3 | 50% | 10% |
| 4 | 25% | 10% |
| Control | 0 | 0 |

Figure 2A:
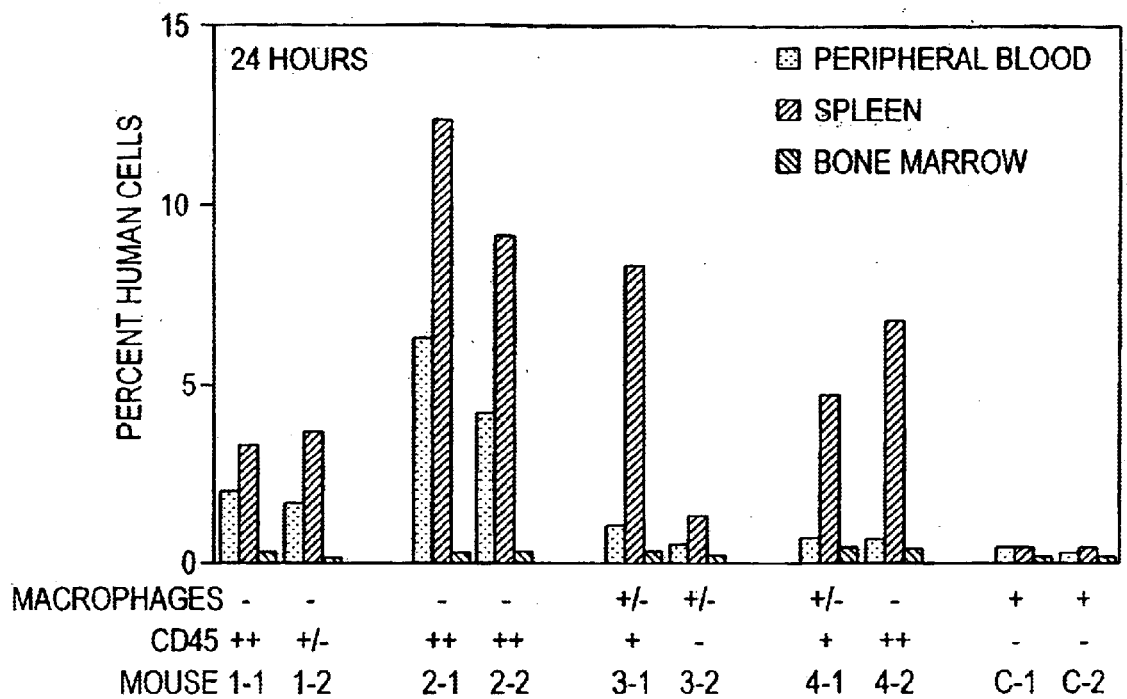
FIG. 2A–B is a summary of flow cytometric data of human cell content in peripheral blood, spleen and bone marrow and of splenic immunocytochemistry. Evaluation for CD45 staining is as follows: (−) no CD45+ cells visible; (+/−) few CD45+ cells in white pulp areas or not all white pulp areas populated; (+) clear presence of CD45+ cells in white pulp areas; and (++) many CD45+ cells in white pulp areas.
Figure 2B:
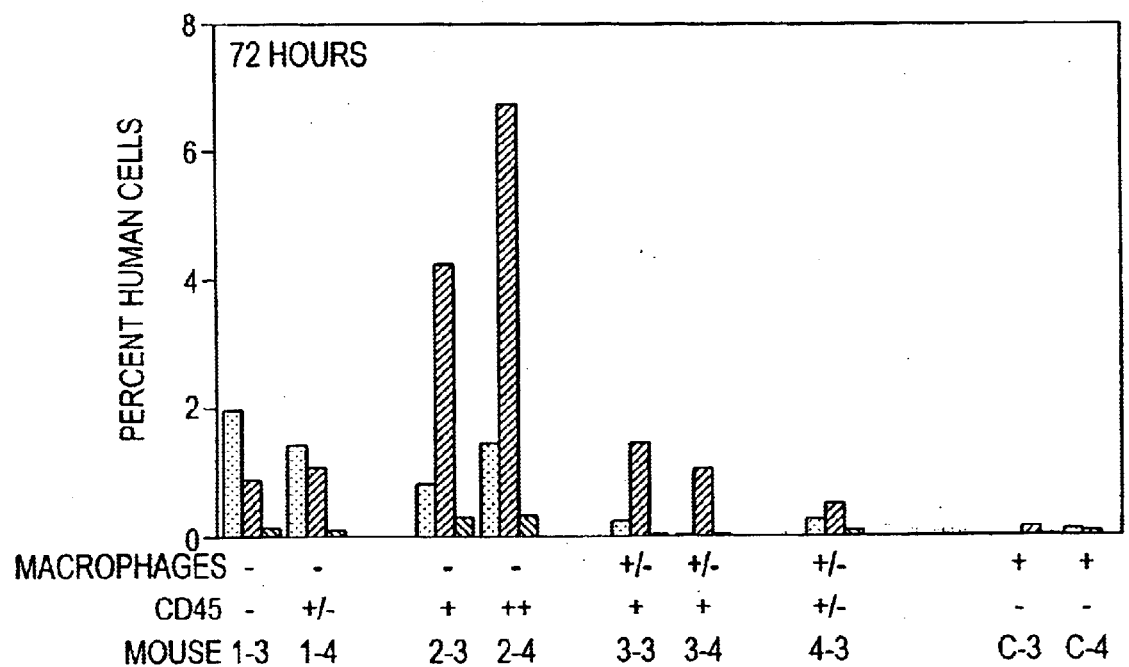

The results obtained are shown in FIGS. 1 and 2. Human cells were detectable at low levels in peripheral blood, spleen and bone marrow of non-treated SCID mice 24 hours after intravenous injection when assayed by FACS as described in Example 4 and demonstrated in FIG. 1 (control, 24 hrs). The cells were completely devoid of detectable cells in these tissues within 72 hours post-injection as demonstrated in FIG. 1, control (72 hrs). In contrast, human cells were detectable at high levels under all titration conditions at both 24 and 72 hours in these tissues, as demonstrated in FIG. 1 (treatment 2).

In order to determine cell distribution, at the time of sacrifice ½ of the spleen was removed, frozen in liquid nitrogen, and stored at −70° C. The effectiveness of macrophage depletion was assessed by enzyme histochemistry for acid phosphatase, and the influx and localization of human cells was determined by using an anti-CD45 antibody as described in Example 4. Evaluations of sections was described as follows for acid phosphatase: (−) red pulp depleted of macrophages; (+/−) severely depleted, but some macrophages detectable in red pulp; and (+) no depletion. Evaluation for CD45 staining was as follows: (−) no CD45$^+$ cells visible; (+/−) few CD45$^+$ cells in white pulp areas or not all white pulp areas populated; (+) clear presence of CD45$^+$ cells in white pulp areas; and (++) many CD45 cells in white pulp areas.

These results are summarized in FIG. 2 and show that a great proportion of human cells reside in the spleen of liposome-encapsulated $Cl_2MDP$ treated animals with levels as high as 12.3% 24 hours post-injection and 6.7% 72 hours post-injection (FIG. 2A, mouse 2–1 and 2B, mouse 2–4 respectively) compared to control mice where maximum levels in the spleen are 0.37% 24 hours. post-transplant (FIG. 2A, mouse C-2) and are undetectable at 72 hours post-transplant. In FIG. 2, the percent human cell value was calculated as the difference between the proportion of cells found positive for W6/32 and CD45 compared to cells in the same quadrant when stained with irrelevant isotype control FITC-conjugated IgG1 (Becton Dickinson) and TC-conjugated IgG2A (Caltag).

Although spleen cell numbers were reduced in treatment 1 mice (2.5×10 and 5×10$^5$ for mice 1–3 and 1–4 respectively) compared to control animals (2.7×10$^6$ and 1.1×10$^6$ for mice C-3 and C-4 respectively) treatment 2 mouse spleen cell content was not greatly altered (7.5×10$^5$ and 1.1×10$^6$ for mice 2–3 and 2–4 respectively). This indicates clearly that the observed retention in the spleen is not a concentration effect due to decrease in murine cell numbers, but is a preferential accumulation and survival of human cells. Under these conditions, human cells are also capable of circulating in the peripheral blood and are detectable in the bone marrow for at least 72 hours.

Splenic cryostat sections stained with acid-phosphatase to detect macrophages show complete elimination of red pulp and marginal zone macrophages with maintenance of some white pulp macrophages in liposome treated animals when compared to controls (FIG. 2, macrophages). Cells staining positive for CD45 are not detectable in cryostat sections of control animals (FIG. 2, CD45), in liposome treated animals. However, accumulation of human cells is found restricted to the white pulp and marginal zones. The extent of elimination of acid phosphatase positive cells in the red pulp region correlates with accumulation of human cells in the white pulp region. This is particularly obvious in treatment 2 mice where red pulp macrophages are completely eliminated, and the concentration of white pulp localized CD45$^+$ cells is the highest. The proportion of human cells in the peripheral blood and the spleen is dependent on the treatment provided. The higher dose treatment regimens (Table 1, treatments 1 and 2) allow human cells to circulate in the peripheral blood for at least 72 hours (FIG. 2 mouse 1–3, 1–4, 2–3, 2–4). The observed effect however is most striking in treatment 2 which is the optimum treatment regimen of those tested for retention of human cells in peripheral blood, spleen and bone marrow.

Example 7
Effects of a Sinfle CL$_2$MDP Dose on the'Number of Human Blood Cells Invading Peripheral Tissues In order to determine if the human cells protected by Cl$_2$MDP treatment were circulating and invading peripheral tissues, SCID-hu Thy/Liv mice were injected in the tail vein with either 200 μl of the liposome-encapsulated Cl$_2$MDP (N =2) or 200 μl of PBS (N =2). On day 4, blood samples were taken for analysis of human cell content by immunophenotyping, as described in Example 4. In addition, the Thy-Liv implants and spleen were removed to quantify human cell content by histological analysis, also as described in Example 6.

The Thy-Liv grafts from both liposome-encapsulated CL$_2$MDP-treated mice and from PBS control mice were essentially all (>99%) human and predominately (approximately 70%) CD4$^+$/CD8$^+$ double positive. While the two PBS control mice and one of the liposome-encapsulated CL$_2$MDP-treated mice demonstrated low levels (0.5 to 1.0%) of human cells in the spleen, the other liposome-encapsulated CL$_2$MDP-treated mouse demonstrated a 5- to 10-fold increase in human cell content in the spleen (5%) as compared with the human cell count observed from the blood samples before and after the liposome-encapsulated Cl$_2$MDP injection (FIG. 2).

Example 8
The Effects of Cl$_2$MDP on the Human Cell Content of Peripheral Blood in SCID-hu Thy/Liv mice In order to determine if a cellular constituent of the spleen is responsible for depletion of human cells, experiments were performed to assess the effect of eliminating endogenous mouse macrophages by treatment of the mice with liposome-encapsulated Cl$_2$MDP.

Figure 3A:
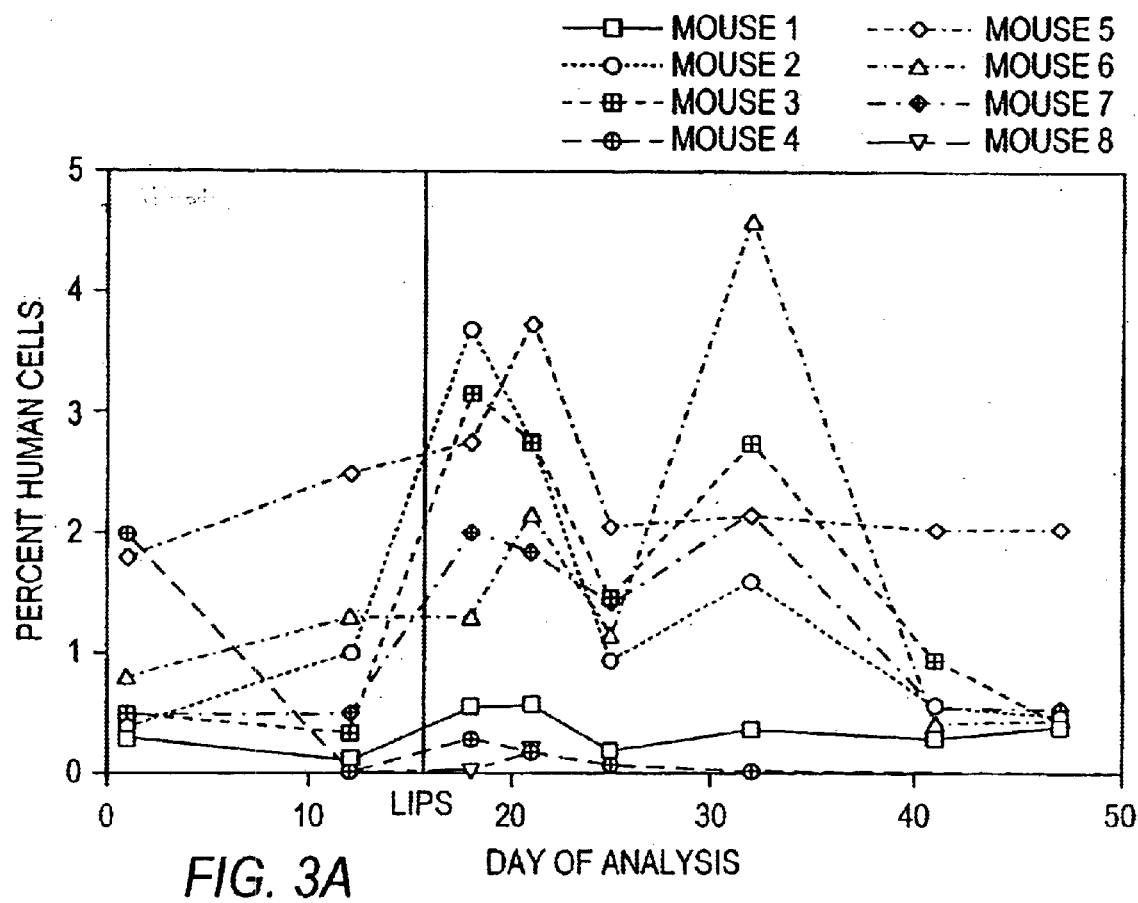
FIG. 3A–B depicts the percent of human cell content in the peripheral blood of SCID-hu Thy/Liv mice over time.

Although the SCID-hu Thy/Liv mice have substantial numbers of human cells in the grafts, the numbers of circulating cells in the periphery remain low. To test whether macrophages play a role in this depletion, SCID-hu Thy/Liv mice transplanted one year previously with fetal liver and thymus were screened for peripheral blood human cell content at days 1 and 12. On day 16, 200 μl of either PBS or liposome-encapsulated Cl$_2$MDP (100% stock) were injected into the tail vein of these mice. Peripheral blood was then collected at days 18, 21, 25, 32, 41 and 47 and analyzed by FACscan for human cell content. Red blood cells were lysed, and the remaining cells stained with W6/32-FITC, CD45-TC and biotinylated mouse pan leukocyte marker monoclonal antibody Ly5.1 with second stage PE-conjugated streptavidin (Becton Dickinson). The percentage of human cells was determined by cells double positive for W6/32 and CD45 and confirmed by being Ly5.1 negative. The results are summarized in FIG. 3.

Figure 3B:
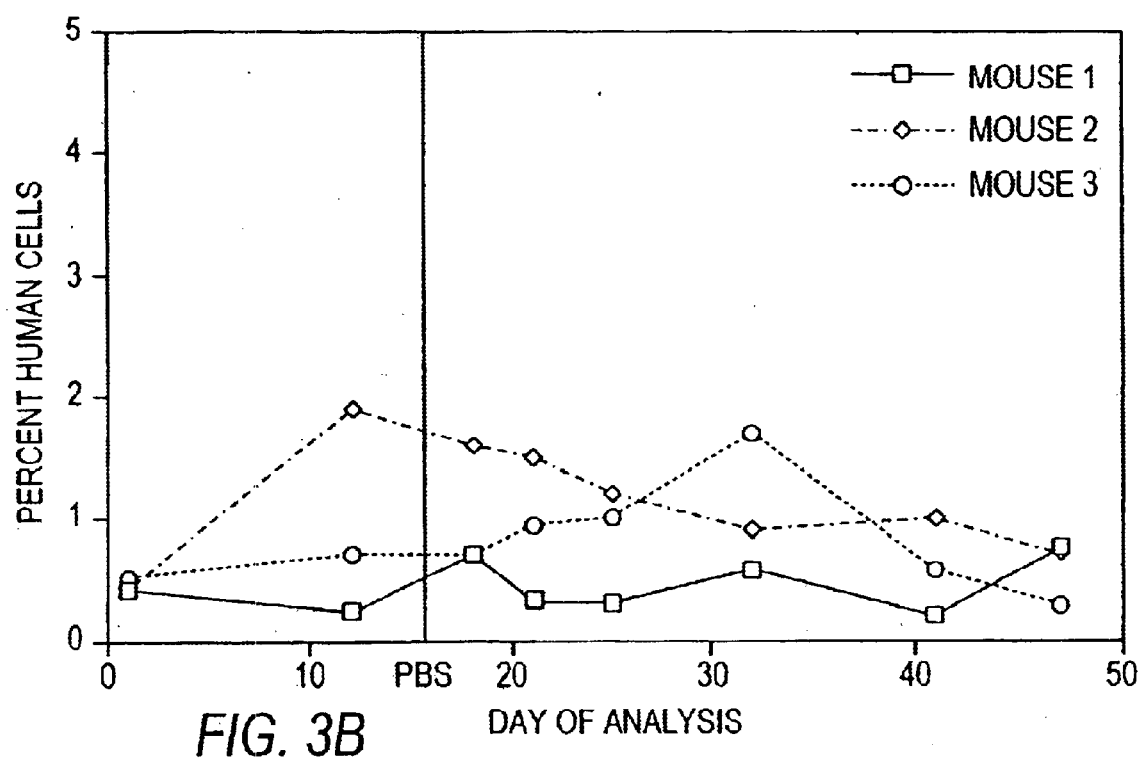

Based on results observed for macrophage recovery in normal (C3D2) Fl mice after liposome treatment, if the decline in human PBLs were due to murine macrophage, then an increase in human cells in the periphery would occur immediately after injection, followed by a return to baseline levels with the recovery of murine macrophages within 1–2 weeks. Van Rooijen et al. (1989). PBS control mice (N=3) did not demonstrate a significant change in levels of human cells in the periphery following injection (FIG. 3B). Five of 8 mice injected with liposomes, however, demonstrated a rise in human cells in the periphery 2–5 days post injection (days 18 and 21, FIG. 3A), which was maintained at least 16 days post injection, and returned to base levels by 25 days post injection. The most striking of these were 2 mice in which human cell content in the peripheral blood rose from 0.3–0.5% pre-treatment to 2.8–3.2% post treatment (mouse 2 and 3, FIG. 3A) and returned to 0.3–0.5% within 25 days post injection.

Example 9
The Effects of Cl$_2$MDP on Macronhage Content in the Spleen of SCID-hu Thy/Liv Mice A number of SCID-hu Thy/Liv mice were also treated with single and multiple injections of liposomes, and sacrificed to determine the efficiency of macrophage depletion in the spleen and correlate this effect with the proportion of human cells in the periphery. Macrophage content in the spleen was assessed by staining cryostat sections for acid phosphatase as described in Example 4. Human cell content was determined by both CD45 staining of cryostat sections and FACS analysis of splenic cells for co-expression of W6/32 and CD45.

SCID mice implanted with Thy/Liv grafts 11–12 months previously were given a treatment of 1 i.v. injection of 0.2 ml or 4 single i.v. injections every 5–7 days of either PBS or 100% stock and sacrificed for analysis 2, 3 or 8 days after the last injection (days after last injection). Prior to sacrifice a sample of tail vein peripheral blood (PB) was taken for flow cytometry. One-half of the spleen was homogenized and used for flow cytometry. Red blood cells were lysed, and cells stained with W6/32-FITC, CD45-TC and biotinylated mouse pan leukocyte marker monoclonal antibody Ly5.1 with second stage PE-conjugated streptavidin. The percentage of human cells positive for both W6/32 and CD45 as determined by analysis on a FAcscan is given (FACS W6/32-CD45). One-half of the spleen was frozen in liquid nitrogen for cryostat sections and immunochemistry as described in Example 6. Murine macrophage and CD45 positive cell contents were also.measured and evaluated as described in Example 6.

The results obtained are presented below in Table 2, where LIPS stands for liposome-encapsulated Cl$_2$MDP and PB stands for peripheral blood.

TABLE 2

| Mouse | Treatment (# of inj) | Days After Last Inj. | Spleen Immuno-chemistry Murine Macs | CD45 | FACS W632-CD45 PB | Spleen |
|---|---|---|---|---|---|---|
| 7732-4 | PBS (1) | 3 | + | − | 0.38 | 1.30 |
| 7732-5 | PBS (1) | 3 | + | − | 0.31 | 0.40 |
| 7732-1 | LIPS (1) | 3 | − | +++ | 0.87 | 5.03 |
| 7732-2 | LIPS (1) | 3 | + | − | 0.14 | 0.43 |
| 7634-4 | PBS (4) | 2 | + | − | ND | 0.14 |
| 7634-5 | PBS (4) | 2 | + | − | ND | 0.01 |
| 7636-5 | PBS (4) | 2 | + | − | ND | 0.28 |
| 7541-5 | LIPS (4) | 2 | +/− | − | ND | 0.00 |
| 7544-2 | LIPS (4) | 2 | − | +++ | ND | 3.43 |
| 7636-3 | LIPS (4) | 2 | − | − | ND | 1.09 |
| 7541-1 | PBS (4) | 8 | + | − | 0.70 | 0.03 |
| 7544-5 | PBS (4) | 8 | + | − | 0.30 | 0.28 |
| 7543-2 | LIPS (4) | 8 | +/− | +/− | 0.86 | 21.60 |
| 7635-3 | LIPS (4) | 8 | − | +++ | 0.81 | 30.69 |

As shown in Table 2, all PBS control mice maintained murine macrophage in the spleen, and had undetectable levels of CD45 staining in cryostat sections. Low levels of human cells were however detected in peripheral blood and spleen by FACS in control mice (up to 1.30%, Table 2, mouse 7732-4), suggesting the level of sensitivity for detection is higher by flow cytometry under these conditions. In all liposome-encapsulated Cl$_2$MDP treated animals where high levels of CD45$^+$ cells were detected in cryostat sections (Table 2, mouse 7732-1, 7544-2, 7635-3), disappearance of acid-phosphatase positive cells in the marginal zone and red pulp of the spleen was also noted.

The most striking examples of this were observed in mice that received 4 sequential injections and were analyzed 8 days after the last injection. Two control PBS mice (Table 2 mouse 7541-1, 7544-5) had low levels of human cells in the peripheral blood and spleen (less than 1.0%), and acid phosphatase positive cells in the spleen. However, the two mice that received liposome treatment demonstrated a large increase in human cell content observed by FACS with 30.69% for mouse 7635-3 in Table 2. Mouse 7635-3 had a 7–12 fold decrease in splenic cell number compared to the 2 control mice, suggesting again as for the PBL injections, that the result observed is due to a preferential accumulation and survival of human cells in the spleen.

Immunohistochemical and flow cytometry evaluation of macrophage depletion and human cell infiltration in liposome-encapsulated $Cl_2MDP$ treated SCID-hu Thy/Liv mice were performed and the results are shown in FIG. 4. A) Cryostat sections of SCID-hu Thy/Liv mice treated with PBS (a and b) or $Cl_2MDP$ liposomes (c and d) and analyzed for acid phosphatase (a and c) or stained with CD45 (b and d) as described in Example 4. wp: white pulp; rp: red pulp of the spleen (magnification: 10× objective). B) Flow cytometry analysis of splenic cells from mouse 7635-3, Table 2. Splenic cells were stained with W6/32-FITC, CD45-TC and Ly5.1-Biotin plus SA-PE as described, or with a combination of CD4-FITC. (Becton Dickinson), CD8-PE (Becton Dickinson) and CD45-TC. Panel A: Forward scatter versus side scatter showing the gated region (R2). Panel B: Isotype control profile of IgG1-FITC and IgG2a-TC staining. Panel C: Profile of cells stained with W6/32-FITC and CD45-TC stained cells. Panel D: Histogram of CD45 staining (solid line) and isotype control (dashed line) with gates set for CD45 positive cells (Ri). Panel E: Histogram of CD8 positive cells after gating on R1 and R2. The percentage of positive cells is indicated in the top right corner. Panel F: Histogram of CD4 positive cells after gating on R1 and R2.

Figure 4A:
FIG. 4A depicts cryostat sections of SCID-hu Thy/Liv mice treated with PBS (a and b) or liposome-encapsulated $Cl_2MDP$ (c and d) and analyzed for acid phosphatase (a and c) or stained with antibodies specific for CD45 (b and d). The following abbreviations are used: wp, white pulp; and rp, red pulp of the spleen.
Figure 4B:
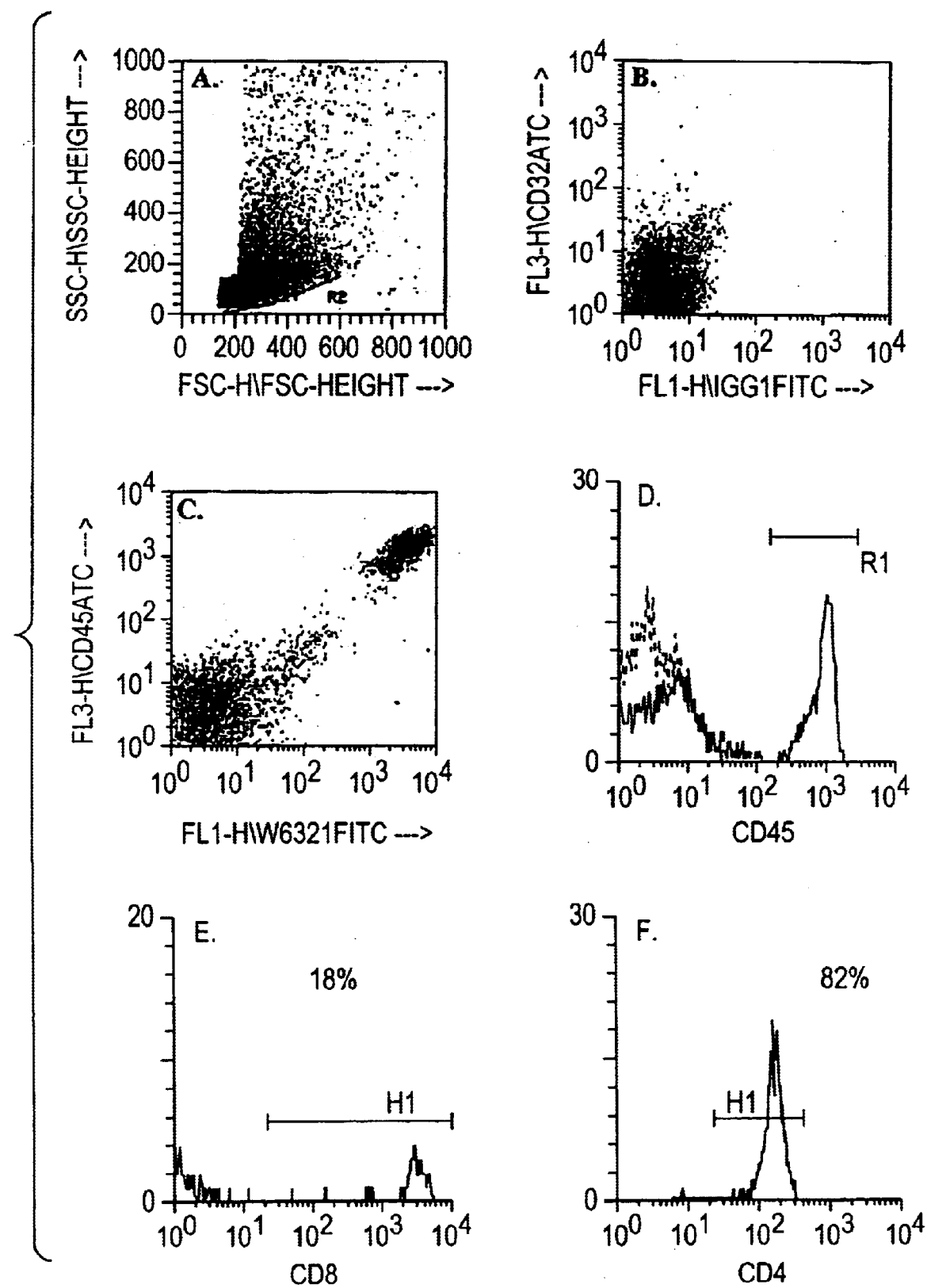
FIG. 4B depicts flow cytometry analyses of splenic cells from mouse 7635-3. Panel A depicts forward scatter versus side scatter showing the gated region (R2). Panel B depicts the isotype control profile of IgGl-FITC and IgG2a-TC staining. Panel C depicts the profile of cells stained with W6/32-FITC and CD45-TC stained cells. Panel D depicts the histogram of CD45 staining (solid line) and isotype control (dashed line) with gates set for $CD45^+$ cells (RI). Panel E depicts the histogram of $CD8^+$ cells after gating on region Rl (panel D) and region R2 (panel A). The percentage of positive cells is indicated in the top right corner. Panel F depicts the histograms of $CD4^+$ cells after gating on Rl and R2.

Staining of cryostat sections show very clearly the effect of liposome mediated depletion on the spleen. In control mice (FIG. 4A, panel a) there is a uniform distribution of acid phosphatase positive cells throughout the white and red pulp area as well as the marginal zone, and these areas are devoid of detectable CD45 positive cells (FIG. 4A, panel b). The liposome treated mice show a near complete depletion of acid phosphatase positive cells in the red pulp and marginal zone (FIG. 4A, panel c) and an accumulation of CD45 positive cells around the central arteriole of the white pulp (FIG. 4A, panel d). Further investigation of. the cell phenotype of mouse 7635-3 is shown in FIG. 4B. Cells gated for low side scatter (FIG. 4B, panel A) show the large percentage of W6/32-CD45 positive cells (FIG. 4B, panel C) compared to antibody controls (FIG. 4B, panel B). Cells that were gated for both low side scatter and expression of CD45 (FIG. 4B, panel D) show a predominance of $CD4^+$ cells (82%, FIG. 4B, panel F), the remainder being $CD8^+$ (18%, FIG. 4B, panel E). These proportions (4:1, CD4:CD8) are within the range observed in peripheral blood of most SCID-hu Thy/Liv mice in our hands, indicating that the infiltrating cell population consists of mature T-cells.

Although the foregoing invention has been described in some detail by way of illustration and example for purposes of clarity of understanding, it will be apparent. to those skilled in the art that certain changes and modifications may be practiced. Therefore, the description and examples should not be construed as limiting the scope of the invention, which is delineated by the appended claims.

We claim:

1. A method of reducing depletion of non-autologous hematopoietic cells in a mammal which lacks functional endogenous B- and T-cells, comprising administering to the mammal an effective amount of dichloromethylene diphosphonate such that the number of endogenous macrophages are decreased to a level effective to reduce depletion of transplanted non-autologous hematopoietic cells.

2. The method according to claim 1 wherein the non-autologous hematopoietic cells are injected into the the mammal.

3. The method according to claim 1, wherein the the non-autologous hematopoietic cells are made by hematopoietic tissue engrafted into the mammal.

4. The method according to claim 1 wherein the mammal is infected with an immunodeficiency virus.

5. The method according to claim 4, wherein the mammal is human and the virus is human immunodeficiency virus.

6. The method according to claim 1 wherein the mammal lacks said endogenous B- and T-cells due to radiation therapy.

7. The method aording to claim 1, wherein the mammal lacks said endogenous B- and T-cells due to chemotherapy.

8. The method according to claim 1, wherein the mammal is selected from the group consisting of a human, a mouse, a SCID/SCID mouse, a SCID-hu mouse, and a CID horse.

9. The method according to claim 8, wherein the mammal is a SCID-hu Thy/Liv mouse.

10. The method according to claim 1, wherein the mammal is transplanted with non-autologous hematopoietic tissue.

11. The method according to claim 2, wherein the mammal is human.

12. A non-human mammal which lacks functional endogenous B- and T-cells, comprising human hematopoletic cells, wherein the non-human mammal contains a decreased level of endogenous macrophages sufficient to reduce depletion of non-autologous hematopoietic cells and wherein the decreased level of endogenous macrophages is achieved by administering to the mammal an effective amount of dichloromethylene diphosphonate.

13. The non-human mammal according to claim 12, wherein the mammal contains engrafted human hematopoietic tissue.

14. The non-human mammal according to claim 13, wherein the non-autologous hematopoietic cells are produced by the engrafted tissue.

15. The non-human mammal according to claim 12, wherein the mammal is selected from the group consisting of a SCID/SCID mouse, a SCID-hu Thy/Liv mouse, and a CID horse.

16. A method of improving or restoring engraftment efficiency for transplantation of a population of non-autologous hematopoietic cells in a host mammal which lacks functional endogenous B- and T-cells, comprising transplanting non-autologous hematopoletic cells into a mammal lacking functional endogenous B- and T-cells in conjunction with administering to the mammal an effective amount of dichloromethylene diphosphonate which decreases the number of endogenous macrophages in the host mammal, thereby improving or restoring the engraft efficiency for transplantation of said non-autologous hematopoietic cells.

17. The method according to claim 16, wherein the mammal is a human infected with human immunodeficiency virus.

18. The method according to claim 16, wherein the mammal is selected from the group consisting of a SCID/SCID mouse, SCID-hu Thy/Liv mouse, and a CID horse.

19. The method according to claim 16, wherein the dicloromethtlene diphosphonate is liposome-encapsulated.

* * * * *